US009795378B2

(12) United States Patent
Nawrocki et al.

(10) Patent No.: US 9,795,378 B2
(45) Date of Patent: Oct. 24, 2017

(54) METHOD FOR APPROXIMATING WOUNDS

(71) Applicant: Ethicon, Inc., Somerville, NJ (US)

(72) Inventors: Jesse Nawrocki, Annandale, NJ (US); Heather Nonnenmann, Warminster, PA (US)

(73) Assignee: Ethicon, Inc., Somerville, NJ (US)

( * ) Notice: Subject to any disclaimer, the term of this patent is extended or adjusted under 35 U.S.C. 154(b) by 250 days.

(21) Appl. No.: 14/530,206

(22) Filed: Oct. 31, 2014

(65) Prior Publication Data
US 2016/0120543 A1    May 5, 2016

(51) Int. Cl.
*A61B 17/06*    (2006.01)
*A61L 17/10*    (2006.01)

(52) U.S. Cl.
CPC ........ *A61B 17/06166* (2013.01); *A61L 17/10* (2013.01); *A61B 17/06066* (2013.01); *A61B 2017/06176* (2013.01)

(58) Field of Classification Search
CPC .... A61B 17/06166; A61B 2017/06176; A61B 17/06066; A61L 17/10
See application file for complete search history.

(56) References Cited

U.S. PATENT DOCUMENTS

| 4,823,794 A * | 4/1989 | Pierce ................. A61B 17/0401 606/232 |
| 5,053,047 A | 10/1991 | Yoon |
| 5,123,913 A | 6/1992 | Wilk |
| 5,219,359 A * | 6/1993 | McQuilkin ........ A61B 17/0401 602/43 |
| 5,222,976 A | 6/1993 | Yoon |
| 5,312,436 A | 5/1994 | Coffey |
| 5,366,480 A * | 11/1994 | Corriveau .......... A61B 17/0401 606/232 |
| 5,403,346 A | 4/1995 | Loeser |
| 5,450,860 A | 9/1995 | O'Connor |

(Continued)

FOREIGN PATENT DOCUMENTS

| EP | 1857236 A1 | 11/2007 |
| EP | 1858243 A1 | 11/2007 |

(Continued)

OTHER PUBLICATIONS

International Search Report for International Application No. PCT/US2012/056858 dated Nov. 29, 2012.

*Primary Examiner* — Julian W Woo
(74) *Attorney, Agent, or Firm* — Melissa J. Szanto

(57) ABSTRACT

A method for approximating a wound using a uni-directional, barbed wound closure device having a needle and a stop element. The method includes taking a first pass by entering intact tissue at a location in proximity to the first apex and exiting in intact tissue at a location away from and above said first apex, pulling the wound closure device until the stop element is seated above the tissue plane, moving back toward the first apex and taking at least a second pass in a direction substantially perpendicular to the first pass at a location above or adjacent to the first apex, moving in a direction toward the second apex, approximating the wound using a continuous suturing pattern, moving toward the first apex, taking at least two passes across the wound, and cutting off a free end of the wound closure device in proximity to a surface of the tissue.

8 Claims, 4 Drawing Sheets

(56) References Cited

U.S. PATENT DOCUMENTS

| | | | |
|---|---|---|---|
| 5,683,417 A | 11/1997 | Cooper | |
| 5,697,950 A | 12/1997 | Fucci | |
| 5,707,394 A | 1/1998 | Miller | |
| 6,033,430 A | 3/2000 | Bonutti | |
| 6,117,139 A | 9/2000 | Shino | |
| RE36,974 E | 11/2000 | Bonutti | |
| 6,241,747 B1 | 6/2001 | Ruff | |
| 6,264,675 B1 | 7/2001 | Brotz | |
| 6,319,263 B1 | 11/2001 | Levinson | |
| 6,599,310 B2 | 7/2003 | Leung et al. | |
| 6,730,112 B2 | 5/2004 | Levinson | |
| 6,773,450 B2 | 8/2004 | Leung et al. | |
| 7,056,331 B2 | 6/2006 | Kaplan et al. | |
| 7,301,112 B1 | 11/2007 | Tsai | |
| 7,371,253 B2 | 5/2008 | Leung et al. | |
| 7,468,068 B2 | 12/2008 | Kolster | |
| 7,731,732 B2 | 6/2010 | Ken | |
| 7,850,700 B2 | 12/2010 | Sakura | |
| 7,850,894 B2 | 12/2010 | Lindh, Sr. et al. | |
| 7,857,829 B2 | 12/2010 | Kaplan et al. | |
| 8,083,770 B2 | 12/2011 | Ruff et al. | |
| 8,142,513 B2 | 3/2012 | Shalon | |
| 8,267,961 B2 | 9/2012 | Popadiuk | |
| 8,506,594 B2 * | 8/2013 | AlGhamdi | A61B 17/06166 606/228 |
| 8,518,078 B2 * | 8/2013 | Sulamanidze | A61B 17/06066 606/144 |
| 8,715,320 B2 | 5/2014 | Lindh, Sr. | |
| 8,721,664 B2 * | 5/2014 | Ruff | A61B 17/04 606/139 |
| 8,747,437 B2 | 6/2014 | Leung et al. | |
| 8,777,988 B2 | 7/2014 | Leung et al. | |
| 8,777,989 B2 | 7/2014 | Leung et al. | |
| 9,095,336 B2 * | 8/2015 | Deng | A61B 17/06166 |
| 9,533,446 B2 * | 1/2017 | Rousseau | B29C 65/08 |
| 2001/0044639 A1 | 11/2001 | Levinson | |
| 2003/0149447 A1 | 8/2003 | Morency | |
| 2004/0122456 A1 | 6/2004 | Saadat | |
| 2005/0004576 A1 | 1/2005 | Benderev | |
| 2005/0049635 A1 | 3/2005 | Leiboff | |
| 2007/0257395 A1 | 11/2007 | Lindh | |
| 2008/0200751 A1 | 8/2008 | Browning | |
| 2008/0234731 A1 | 9/2008 | Leung et al. | |
| 2008/0281357 A1 | 11/2008 | Sung et al. | |
| 2008/0312688 A1 | 12/2008 | Nawrocki et al. | |
| 2009/0018577 A1 | 1/2009 | Leung | |
| 2009/0076547 A1 | 3/2009 | Sugimoto | |
| 2009/0248067 A1 | 10/2009 | Maiorino | |
| 2009/0248070 A1 | 10/2009 | Kosa et al. | |
| 2009/0312791 A1 | 12/2009 | Lindh, Sr. et al. | |
| 2010/0084780 A1 | 4/2010 | Lindh, Sr. | |
| 2010/0146770 A1 | 6/2010 | Morency et al. | |
| 2010/0211098 A1 | 8/2010 | Hadba et al. | |
| 2010/0274283 A1 * | 10/2010 | Kirsch | A61B 17/0401 606/228 |
| 2010/0298871 A1 | 11/2010 | Ruff et al. | |
| 2010/0298880 A1 | 11/2010 | Leung et al. | |
| 2010/0318123 A1 | 12/2010 | Leung et al. | |
| 2011/0054522 A1 | 3/2011 | Lindh, Sr. et al. | |
| 2011/0093010 A1 | 4/2011 | Genova | |
| 2011/0106152 A1 | 5/2011 | Kozlowski | |
| 2012/0016183 A1 | 1/2012 | Gellman | |
| 2012/0046525 A1 | 2/2012 | Russell | |
| 2013/0085525 A1 | 4/2013 | Nawrocki | |
| 2014/0100607 A1 | 4/2014 | Broom | |

FOREIGN PATENT DOCUMENTS

| | | |
|---|---|---|
| EP | 1857236 B1 | 11/2009 |
| EP | 1858243 B1 | 11/2009 |
| EP | 1867288 B1 | 4/2010 |
| GB | 1091282 A | 11/1967 |
| WO | WO 2009020795 A1 * | 2/2009 |
| WO | WO 2010051506 A1 | 5/2010 |
| WO | WO 2013048947 A1 | 4/2013 |

* cited by examiner

continued …

METHOD FOR APPROXIMATING WOUNDS

FIELD OF THE INVENTION

The present invention relates generally to the field of medical devices, and more particularly to methods for using suture devices for approximating wounds.

BACKGROUND

Many wounds and surgical incisions are closed using surgical sutures or some other surgical closure device. Barbed sutures are well known and have recently been gaining attention for various medical applications. Typically, barbed sutures are constructed with a series of "barbs" or "protrusions" (used interchangeably herein) that extend outwardly from the suture and function to increase the holding strength of the suture and/or eliminate the need for knot tying. The size and shape of the barbs have practical limitations in a surgical setting.

Barbed sutures are available as both "uni-directional" and "bi-directional" in design. Bi-directional barbed sutures have barbs in two opposing directions on each side of a central region, with needles at both the first and second ends. Typically, closure using these devices starts in the center of the incision, and each half of the incision is closed by stitching from the center outwards towards the ends using the respective first and second needles. Uni-directional barbed suture devices have all of the anchors or barbs facing in one direction, and a needle only at a first end. These devices are applied from one end of the incision to the other.

Some uni-directional barbed sutures include an anchor, tab, loop or the like on the distal end of the suture to provide a "stop" that contributes to the holding strength of the suture and eliminates the need to tie knots to secure the suture on initiation of the closure. The term "stop element" is used herein to refer to any such element regardless of design or type. One such device is disclosed in pending U.S. patent application Ser. No. 13/248,542, filed on Sep. 29, 2011 (Publication No. US2013/0085525), which is incorporated herein by reference in its entirety. With sutures of this type, however, in certain instances and when placed in certain ways, users have been known to pull too hard on the suture and exceed the holding strength of the stop element or compromise the integrity of the stop element. The present invention provides an improved method for using a uni-directional barbed suture having a stop element by which the holding strength of the suture can be greatly increased.

SUMMARY OF THE INVENTION

The present invention provides a method for approximating a wound defined by first and second opposing edges joined at one end at a first apex and joined at an opposite end by a second apex, using a uni-directional, barbed wound closure device having a needle coupled to a proximal end and a stop element at a distal end. The method includes taking a first pass with the needle by entering intact tissue at a location in proximity to the first apex, and exiting in intact tissue at a location away from and above the first apex; pulling the wound closure device through the path defined by the first pass until the stop element is seated above the tissue plane; moving the needle in a direction back toward the first apex and taking at least a second pass in a direction substantially perpendicular to the first pass at a location above or adjacent to the first apex; moving in a direction toward the second apex, proceeding to approximate the wound using a continuous suturing pattern; moving in a direction toward the first apex, taking at least two passes across the wound; and cutting off a free end of the wound closure device in proximity to a surface of the tissue.

The wound closure device may be made of a polymeric material, and may further be an absorbable material such as polydioxanone.

In one embodiment, the stop element is a substantially planar tab element having a length and width, wherein the length is greater than the width.

Also provided is a method for approximating a wound defined by first and second opposing edges joined at one end at a first apex and joined at an opposite end by a second apex, using a wound closure device having a needle coupled to a proximal end and a stop element at a distal end. The method includes taking a first pass with the needle by entering intact tissue at a location above the first apex, and exiting in intact tissue at a location further away from and above the first apex; pulling the wound closure device through the path defined by the first pass until the stop element is seated; moving the needle in a direction back toward the first apex and taking at least a second pass in a direction substantially perpendicular to the first pass at a location above the first apex; moving in a direction toward the second apex, proceeding to approximate the wound using a continuous suturing pattern; moving in a direction toward the first apex, taking at least two passes across the wound; and cutting off a free end of the wound closure device in proximity to a surface of the tissue.

These and other objects, features and advantages of the present invention will be apparent from the following detailed description of illustrative embodiments thereof, which is to be read in connection with the accompanying drawings.

DETAILED DESCRIPTION

Figure 1:
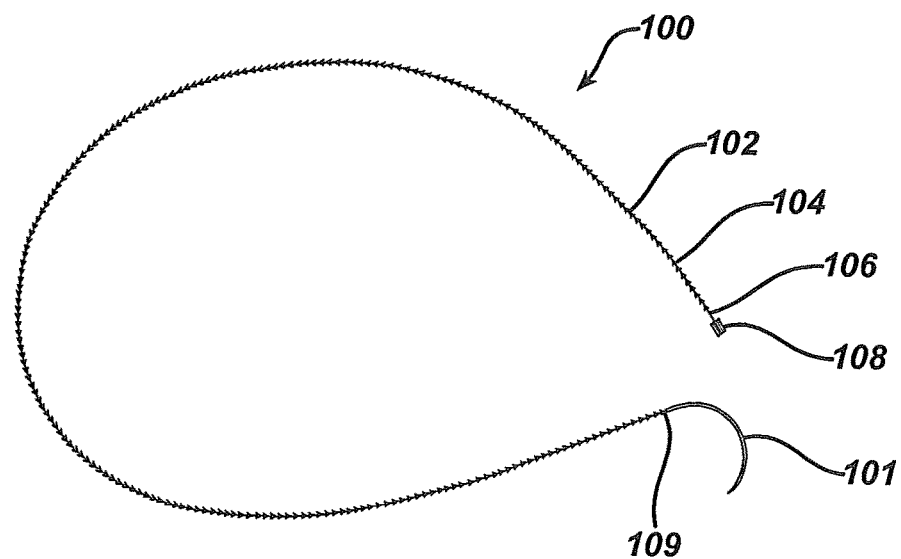
FIG. 1 illustrates a uni-directional wound closure device that can be used in accordance with the methods of the present invention.
Figure 2:
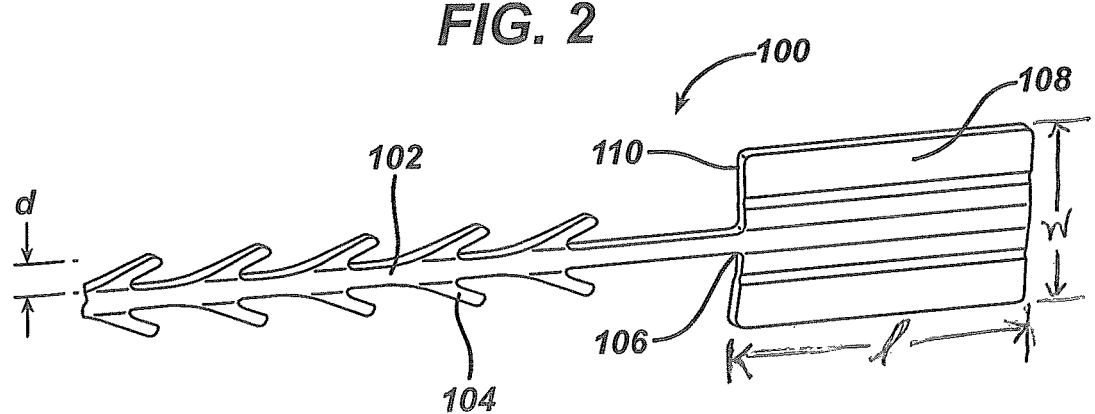
FIG. 2 is an enlarged view of the stop element of the wound closure device of FIG. 1.

FIG. 1 illustrates an exemplary embodiment of a wound closure device 100, such as a uni-directional barbed suture device, that may be used in accordance with the methods of the present invention. The wound closure device 100 includes a filamentary element 102 comprised of any suitable surgical suture material (i.e., absorbable and non-absorbable polymeric materials, metallic, or ceramic materials) that preferably includes a plurality of barbs 104 that extend outwardly therefrom. The suture may be formed by any suitable method, including cutting into the suture shaft to form the barbs, but preferably is compound profile punched from preformed material in a manner described in more detail in U.S. Pat. No. 7,850,894, which is incorporated herein by reference in its entirety. The proximal end 109 of the wound closure device may be coupled to a needle or other insertion device 101. At the distal end 106 of the wound closure device is a stop element or the like 108. The stop element 108 has a leading edge 110, and has a length l and a width w as is better illustrated in FIG. 2.

As indicated previously, using known stitching techniques users, such as surgeons, have been known to place too much tension on the suture, the entire load of which is ultimately directed to the stop element 108. The method described below greatly increases the holding strength of this exemplary uni-directional barbed suture or any such suture having a stop element of any sort on the end.

Figure 3:
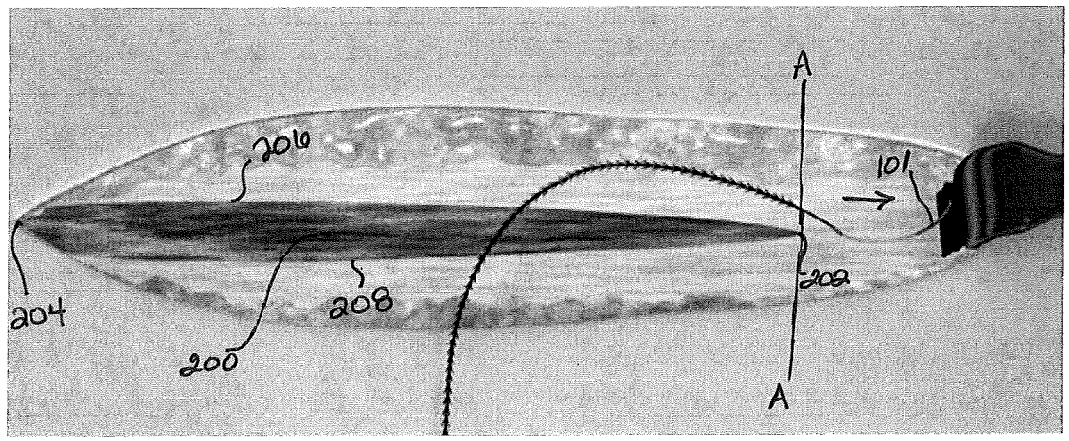
FIGS. 3-7 illustrate steps of an exemplary method for tissue approximation according to the present invention.
Figure 8:
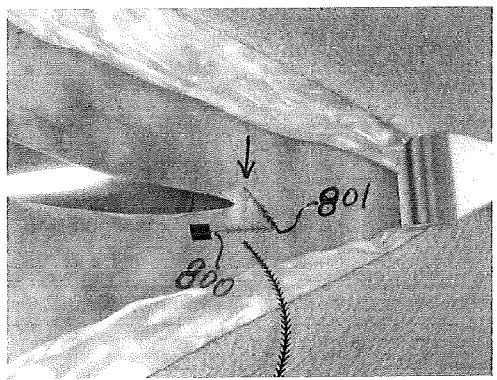
FIG. 8 illustrates an alternative step to the method of FIGS. 3-7.

Referring now to FIG. 3, a wound 200 is shown and is defined by first and second opposing edges 206, 208 that come together on each respective end at a first apex 202 and a second apex 204. To initiate approximation (meaning initial steps taken before actual closing of the wound starts to occur), a first pass is taken with the needle 101 attached to the wound closure device such that the needle enters intact tissue (tissue not compromised by the wound or incision) in proximity to the first apex, and continues along a path leading away from the apex, such as in the direction shown by the arrow in FIG. 3. Preferably, the needle first enters the tissue at a location above the apex and continues further away as shown. In the alternative, such as when space is limited (i.e., knee replacement), the needle may enter the tissue behind, but in proximity to the apex as shown by location 800 in FIG. 8, and continue in a direction away from the apex so long as it exits the tissue at a location sufficiently above the apex (i.e., location 801) so that there is adequate space to perform the perpendicular stitch described below above the apex. For sake of clarity, the term "above" the apex is used to describe a location to the right of line A-A that extends through the apex and substantially perpendicular to the incision line shown in FIG. 3, whereas the term "behind" the apex is used to describe a location to the left of line A-A.

Figure 5:
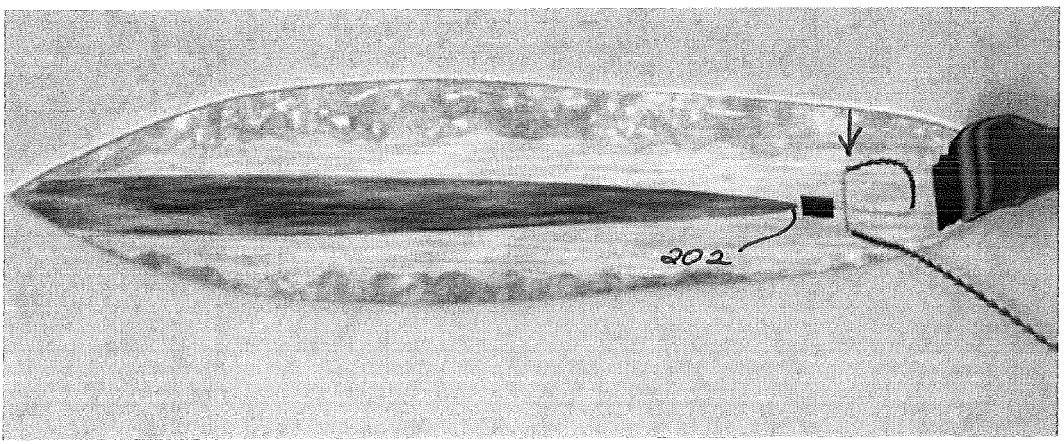

The wound closure device 100 is then passed through the tissue until the stop element 108 is gently seated against the tissue. Preferably, the stop element should be seated above the tissue plane and visible as shown. Then, moving in a direction back toward the first apex but still within the intact tissue above the apex, at least one second pass is taken substantially perpendicularly to the first pass, as shown generally by the arrows in FIGS. 5 and 9. More than one such pass may be taken at the preference of the user.

Figure 6:
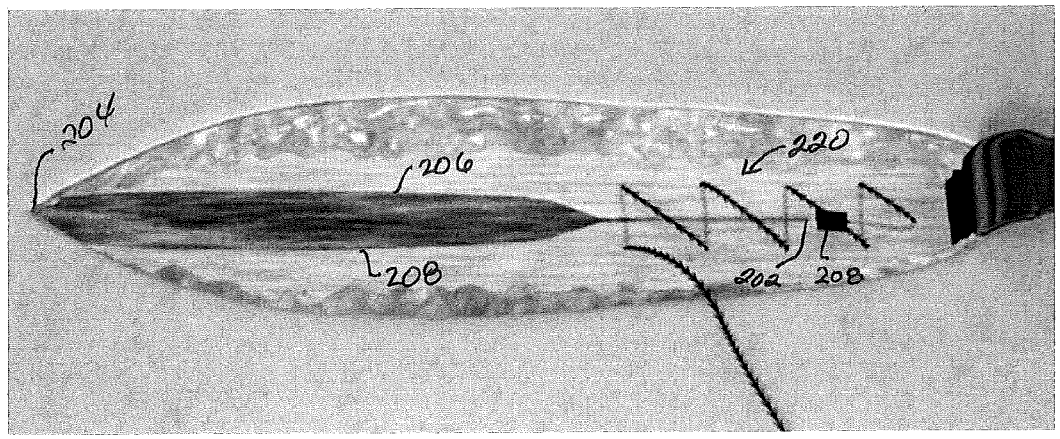

Once this is accomplished, the user can proceed in a direction toward the second apex with a traditional, well known continuous suturing pattern 220 to close the incision, taking apposing bites on either side of the wound in standard fashion and as shown in FIG. 6. To achieve the desired approximation and tension, the user can gently pull on the wound closure device with each tissue passage, with the previous steps performed upon initiation greatly reducing the chance that the full brunt of such tensioning or over tensioning will be incurred by the stop element.

Figure 7:
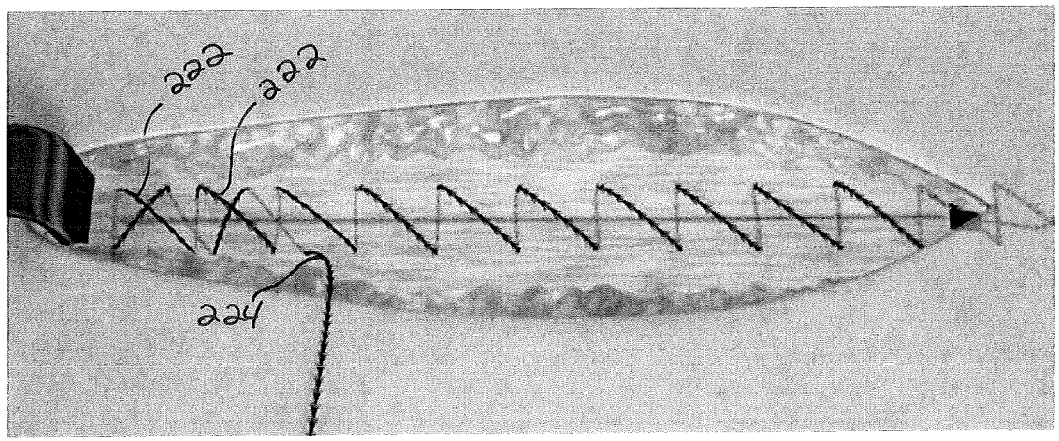

To complete and secure the closure, at least one, and preferably two passes 222 are taken in the reverse direction (i.e., back toward the first apex) across the incision as shown in FIG. 7. The user then gently pulls on the free end of the wound closure device and cuts off the end substantially flush with the surface of the tissue such as at location 224 shown in FIG. 7.

Figure 4:
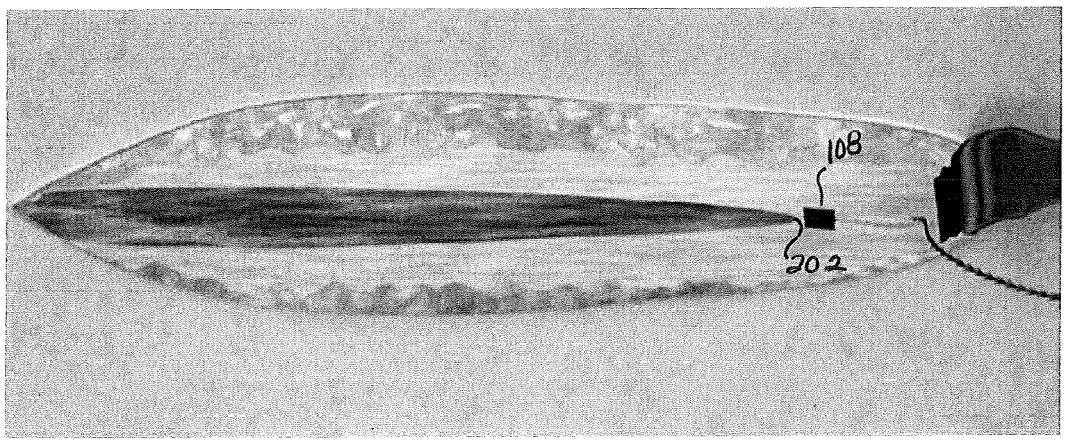
Figure 9:
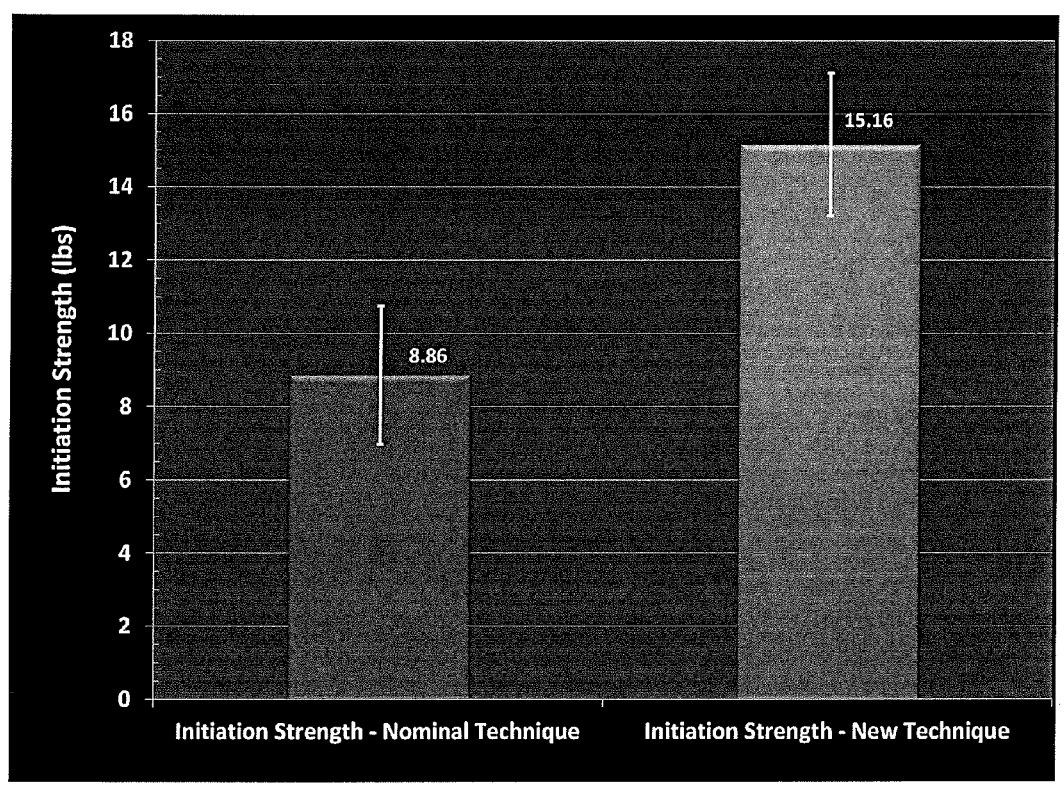
FIG. 9 is a chart illustrating superior holding strength using the method of the present invention.

By taking the first two passes as specifically described herein to initiate the approximation, the wound closure device is more securely "locked" in place, which greatly enhances the holding strength of the wound closure device as compared to other known continuous suturing techniques where the stitching is initiated and immediately continues in the same general direction until the approximation is completed. Further, the greater holding strength during initiation provides more even distribution of load along the length of the closure. Since the anchors are oriented in one direction, the tissue can slide easily over the anchors in the direction of the initiation end. This inherently can allow more load to be put on the end effector. The initiation technique described here relives some of the stress put on the initiation end and better balances the closure between the initiation and termination ends. The table shown in FIG. 9 illustrates the increased holding strength achieved by the method described above. The test was conducted in porcine midline fascia using a knotless fixation device as described above and illustrated in FIGS. 1 and 2, and which was made from polydioxanone and considered a size 1 suture. The baseline ("nominal") technique placed the stop element under the tissue beyond the apex of the closure. In other words, the needle enters from the underside of the tissue and exits above the tissue plane leaving the end effector below the tissue plane. Then one pass is made to begin to approximate the incision with no locking stitch. The method of the present invention ("new technique") for comparison performed the steps described above in conjunction with FIGS. 3-5, and similarly made one pass of tissue approximation to begin to close the incision. In both cases, the free end of the wound closure device was then pulled and the maximum load at failure was recorded. As can be seen in FIG. 9, the new initiation technique described herein provides a significant increase in the holding strength of the device (approximately 71% greater) over the baseline technique.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A method for approximating a wound defined by first and second opposing edges joined at one end at a first apex and joined at an opposite end by a second apex, using a uni-directional, barbed wound closure device extending along a longitudinal axis and having a needle coupled to a proximal end and a substantially planar stop element at a distal end, wherein the stop element has a length extending along said longitudinal axis and width, and wherein the length is greater than the width, comprising:

taking a first pass with said needle by entering intact tissue at a location in proximity to said first apex, and exiting in intact tissue at a location further away from and above said first apex on a tissue plane;

pulling the wound closure device through the path defined by the first pass until the stop element is seated above the tissue plane;

moving the needle in a direction back toward the first apex and taking at least a second pass in a direction substantially perpendicular to the first pass at a location above or adjacent to the first apex and above the stop element on the tissue plane;

moving in a direction toward the second apex, proceeding to approximate the wound using a continuous suturing pattern;

moving in a direction toward the first apex, taking at least two passes across the wound; and cutting off a free end of the wound closure device in proximity to a surface of the tissue.

2. The method according to claim 1, wherein the wound closure device is comprised of a polymeric material.

3. The method according to claim 2, wherein the polymeric material is an absorbable material.

4. The method according to claim 3, wherein the absorbable material is polydioxanone.

5. A method for approximating a wound defined by first and second opposing edges joined at one end at a first apex and joined at an opposite end by a second apex, using a wound closure device extending along a longitudinal axis and having a needle coupled to a proximal end and a stop element at a distal end, wherein the stop element has a length extending along said longitudinal axis and a width, and wherein the length is greater than the width, comprising:

taking a first pass with said needle by entering intact tissue at a location on a surface of tissue above said first apex, and exiting in intact tissue at a location on the surface of tissue further away from and above said first apex;

pulling the wound closure device through the path defined by the first pass until the stop element is seated;

moving the needle in a direction back toward the first apex and taking at least a second pass in the tissue and in a direction substantially perpendicular to the first pass at a location above the first apex and above the stop element;

moving in a direction toward the second apex, proceeding to approximate the wound using a continuous suturing pattern;

moving in a direction toward the first apex, taking at least two passes across the wound; and cutting off a free end of the wound closure device in proximity to a surface of the tissue.

6. The method according to claim 5, wherein the wound closure device is comprised of a polymeric material.

7. The method according to claim 6, wherein the polymeric material is an absorbable material.

8. The method according to claim 7, wherein the absorbable material is polydioxanone.

* * * * *